US008256307B2

United States Patent
Graze, Jr. et al.

(10) Patent No.: US 8,256,307 B2
(45) Date of Patent: Sep. 4, 2012

(54) PARTICULATE SAMPLING SYSTEM AND METHOD OF REDUCING OVERSAMPLING DURING TRANSIENTS

(75) Inventors: Russell R. Graze, Jr., Dunlap, IL (US); Linda M. Riedlinger, Creve Coeur, IL (US); Jerry K. Randall, East Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 946 days.

(21) Appl. No.: 12/288,962

(22) Filed: Oct. 24, 2008

(65) Prior Publication Data

US 2010/0101302 A1    Apr. 29, 2010

(51) Int. Cl.
*G01N 1/22* (2006.01)

(52) U.S. Cl. .................... 73/863.86; 73/23.31

(58) Field of Classification Search ............ 73/23.31, 73/863.86
See application file for complete search history.

(56) References Cited

U.S. PATENT DOCUMENTS

| | | | |
|---|---|---|---|
| 3,511,099 A * | 5/1970 | Harsha | 73/863.11 |
| 4,091,835 A * | 5/1978 | Frampton | 73/863.51 |
| 5,058,440 A | 10/1991 | Graze, Jr. | |
| 5,604,319 A | 2/1997 | Kohsaka et al. | |
| 6,062,092 A | 5/2000 | Weaver | |
| 6,427,543 B1 | 8/2002 | Torrison | |
| 6,615,677 B2 | 9/2003 | Dickson et al. | |
| 7,299,690 B2 | 11/2007 | Graze, Jr. | |
| 7,406,885 B2 | 8/2008 | Graze, Jr. | |
| 2002/0166365 A1 * | 11/2002 | Kogure et al. | 73/28.01 |
| 2007/0068236 A1 * | 3/2007 | Wei et al. | 73/117.3 |
| 2009/0211351 A1 * | 8/2009 | Colvin et al. | 73/114.76 |

* cited by examiner

*Primary Examiner* — Hezron E Williams
*Assistant Examiner* — Nashmiya Fayyaz
(74) *Attorney, Agent, or Firm* — Liell & McNeil (57) ABSTRACT

Testing of engine particulate matter production during a transient is made more accurate by selecting an appropriate sized opening for a test probe of the sampling system located in the exhaust line upstream from a particulate trap. By examining the pressure signature at the test probe location and utilizing that information in conjunction with a desired volumetric flow rate into the sampling system, a flow opening size for the test probe can be selected that reduces potential oversampling which may be otherwise induced due to the back pressure increases in the exhaust line caused by the presence of the particulate trap. The flow opening into the test probe of the sampling system behaves relative unrestricted when pressure differentials at the test probe location are relatively low, such as during steady state operating conditions, but restricts flow into the sampling system when pressure differentials are relatively high, such as at a pressure during a transient event.

19 Claims, 8 Drawing Sheets

Figure 9 ion of exhaust gas being extracted from the power source exhaust flow relative to the total flow of exhaust. Although the system changes this proportion based on changes in the exhaust flow of the power source, the system uses the pressure differential between the exhaust gas flow stream and the pressure inside a sampling probe for feedback. As a result, the system of the '092 patent does not take into account variations in the combined flow seen by the filter when determining the amount of exhaust flow to extract, which can again lead to oversampling and inaccurate results. Such variations may be caused by, for example, exhaust flow excursions and/or other system based factors.

The systems and methods of the present disclosure are directed to overcome one or more of the problems set forth above.

PARTICULATE SAMPLING SYSTEM AND METHOD OF REDUCING OVERSAMPLING DURING TRANSIENTS

TECHNICAL FIELD

The present disclosure relates generally to a proportional exhaust sampling system and method, and more particularly to a strategy for reducing oversampling of exhaust, especially during transient operating conditions of a power source.

BACKGROUND

Exhaust emissions from motorized on-highway machines are regulated by the federal government and must not exceed certain contaminant levels as set forth in Title 40, Chapter 1 of the Code of Federal Regulations, Section 86 Subpart C. For example, some government regulations place limits on the amount of particulate matter that may be emitted by diesel truck engines. These regulations specify the acceptable level of particulate matter that may be carried in the exhaust gas stream of the engine. Particulate matter may include, for example, carbon particulates, unburned hydrocarbons, and sulphates. Initial regulations primarily addressed particulate matter levels when the engine was operating in a relatively steady state condition. More recent regulations have been promulgated that regulate the amount of particulate matter when the engine is undergoing a transient condition, such as accelerating from one speed and load condition to another speed and load.

Due to these regulations, equipment has been developed to test and analyze machine engines and/or other power sources for conformance with government standards. In particular, partial flow exhaust gas sampling systems have been developed in an effort to certify such power sources as being in compliance with government emissions regulations. Generally, these systems operate by extracting a small portion of a power source exhaust flow via a test probe located in the exhaust stack. A regulated flow of filtered ambient air is then mixed with the extracted portion, and the combined flow is directed to a filter configured to trap the particulate matter contained within the combined flow. The power source may then be evaluated based on the quantity of particulate matter trapped by the filter during a particular test cycle. One particulate sampling system and method that has performed well in recent years is shown and described in co-owned U.S. Pat. No. 7,299,690. However, with the onset of additional regulations for testing exhaust for particulate matter content during transient conditions, new previously unaddressed problems have arose. For instance, because of certain system parameters including a fixed flow area opening on the test probe as well as other phenomenon, such as the pressure rise in the exhaust stack during accelerating transient conditions, current systems tend to oversample during pressure increases in the exhaust stack which can lead to an inaccurate assessment of particulate matter production during the transient.

Another such system is described in U.S. Pat. No. 6,062,092 to Weaver ("the '092 patent). The system of the '092 patent utilizes a feedback arrangement to change the proportion of exhaust gas being extracted from the power source exhaust flow relative to the total flow of exhaust. Although the system changes this proportion based on changes in the exhaust flow of the power source, the system uses the pressure differential between the exhaust gas flow stream and the pressure inside a sampling probe for feedback. As a result, the system of the '092 patent does not take into account variations in the combined flow seen by the filter when determining the

SUMMARY OF THE INVENTION

In one aspect, a method of operating an exhaust sampling system includes flowing exhaust into a test probe positioned in an exhaust stack. Flow into the test probe is unrestricted when a pressure differential between the exhaust stack at a probe location and atmospheric pressure is small, but flow into the test probe is restricted when the pressure differential is large.

In another aspect, a method of reducing oversampling of exhaust with an exhaust sampling system during a transient includes a step of restricting flow into sampling system when pressure at a test probe location increases. The restricting step is accomplished by positioning an orifice in a flow path into the test probe.

In still another aspect, a test cell includes a power source fluidly connected to an exhaust line. An exhaust sampling system includes a test probe with a flow opening positioned in the exhaust line for receiving exhaust flow originating from the power source. The flow opening has a flow area size based upon a desired flow rate into the exhaust sampling system and a pressure differential magnitude associated with a transient operating condition of the power source.

DETAILED DESCRIPTION

Figure 1:
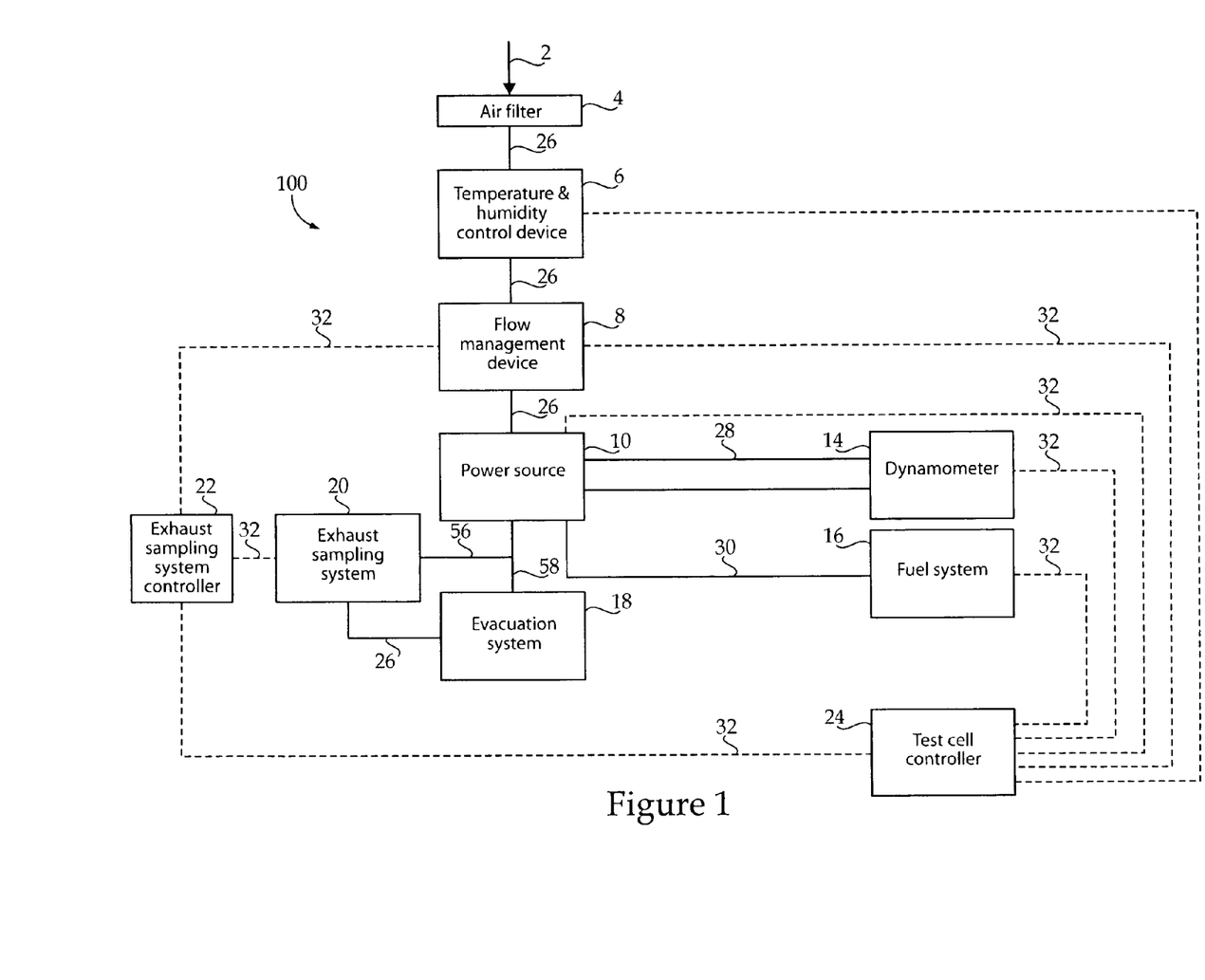
FIG. 1 is a diagrammatic illustration of a test cell according to an exemplary embodiment of the present disclosure.

FIG. 1 illustrates a test cell 100 according to an exemplary embodiment of the present disclosure. The test cell 100 includes a power source 10 mechanically and electrically coupled, and/or otherwise connected to a dynamometer 14. An air filter 4, a temperature and humidity control device 6, and a flow management device 8 may also be fluidly connected to, for example, an intake manifold of the power source 10. In addition, an exhaust manifold or other exhaust release device of the power source 10 may be fluidly connected to an evacuation system 18 of the test cell 100. The evacuation system 18 may include, for example, an exhaust fan and/or one or more filters configured to extract, for example, particulates and/or other harmful pollutants. The evacuation system 18 may also include, for example, a vacuum source or other device configured to act on exhaust gases from the power source 10 and/or the exhaust sampling system 20. The evacuation system 18 may be configured to release the exhaust gases to the environment.

As shown in FIG. 1, an exhaust sampling system 20 may be fluidly and/or otherwise connected to the power source 10, and an extraction component or test probe 56 of the exhaust sampling system 20 may be configured to extract a portion of an exhaust flow of the power source 10. The exhaust sampling system 20 may include an exhaust sampling system controller 22 disposed within the test cell 100 and electrically connected to components of the exhaust sampling system 20 and/or the test cell 100. For example, the exhaust sampling system controller 22 may be configured to communicate electrically with the flow management device 8 and/or a test cell controller 24. As shown in FIG. 1 the power source 10 may also be fluidly connected to a fuel system 16 configured to supply fuel to the power source 10. Although not shown in FIG. 1, it is understood that the fuel system 16 may include, for example, a fuel pump, a fuel tank, a flow meter, a plurality of valves, and/or other conventional components configured to supply a regulated flow of fuel to the power source 10. These components may also be configured to measure, for example, the quantity, flow rate, and/or other characteristics of the flow of fuel supplied to the power source 10.

One or more of the components discussed above may be connected to each other via a flow line 26. For example, the air filter 4 may be connected to the temperature and humidity control device 6 via a flow line 26, and the temperature in humidity control device 6 may be connected to the flow management device 8 via a flow line 26. The fuel system 16 may be connected to the power source 10 via a fuel line 30 and the power source 10 may be connected to the evacuation system 18 via an exhaust line 58. In an exemplary embodiment, the fuel line 30 and the exhaust line 58 may be flow lines 26. The extraction component or test probe 56 of the exhaust sampling system 20 may be connected to, and positioned in, the exhaust line 58, and the extraction component 56 may be configured to extract a portion of an exhaust flow of the power source 10 passing through the exhaust line 58. The exhaust sampling system 20 may also be connected to the evacuation system 18, which vents to atmosphere, via a flow line 26, and the exhaust sampling system 20 may be configured to direct a flow of fluid to the evacuation system 18 during and/or after a sampling cycle. The power source 10 may also be connected to the dynamometer 14 via a mechanical and/or other conventional link 28.

As illustrated in FIG. 1 the temperature and humidity control device 6, the flow management device 8, the power source 10, the dynamometer 14, the fuel system 16, and/or the exhaust sampling system controller 22 may be electrically connected to the test cell controller 24 via control lines 32. In addition the flow management device 8 may be electrically connected to the exhaust sampling system controller 22 via a control line 32. The control lines 32 may enable each of the above components to communicate and/or otherwise send sensed information, control signals, and/or other electrical signals to the test cell controller 24 and/or the exhaust sample system controller 22. The control lines 32 may also enable the test flow controller 24 and/or the exhaust sampling system controller 22 to send control signals to each of the connected components.

The power source 10 illustrated in FIG. 1 may be, for example, any spark ignition engine, diesel engine, and/or other combustion power source known in the art. The dynamometer 14 may be any conventional device used to measure, for example, rpm, torque, and/or other power source operating characteristics from which the output power produced by the power source can be calculated. The air filter 4 may be any conventional filter device configured to, for example, capture and/or otherwise trap dirt and other airborne particles before such particles pass to the power source 10 Such particles may cause damage to, for example, power source cylinders, walls, pistons and piston rings. The air filter 4 may include, for example, a replaceable filter element configured to assist in the capture and/or removal of airborne particles.

The exhaust sampling system controller 22 and/or the test cell controller 24 may be, for example, a central processing unit, an electronic control module, a computer, a radio transmitter, or any other type of controller known in the art. The controllers 22, 24 may be connected to an operator interface (not shown) such as, for example, a keyboard, monitor, printer, touch screen, control panel, or any other device enabling a user to enter commands and/or receive sensed and/or calculated information from components of the test cell 100 and/or the exhaust sampling system 20. In an exemplary embodiment, the controllers 22, 24 may control aspects of the power source test/certification cycle and may be configured to store information for later retrieval and use.

The temperature and humidity control device 6 may be configured to sense and/or control the temperature and/or humidity of the filtered ambient air before it enters the power source 10. The temperature and humidity control device may include, for example, a thermocouple, a hygrometer, a heat exchanger, and/or other conventional components configured to assist in sensing and/or controlling temperature and humidity. The flow management device 8 may be any device or combination of devices configured to measure and/or regulate, for example, the flow rate, pressure, and/or other flow characteristics of a fluid flow. In an exemplary embodiment, the flow management device 8 may include a laminar flow element and/or a pressure differential transducer configured to sense changes in the pressure and/or flow rate of a fluid passing through the flow management device 8 and/or other components of the test cell 100. Each of the test cell components discussed above is known in the art and these components will not be discussed in further detail in the present disclosure. Further, it is understood that each of the dash lines in FIG. 1 illustrate a control line 32 and that each of the solid lines in FIG. 1 represents a flow line 26 with the exception of the extraction component 56, the exhaust line 58, and the link 28.

Figure 2:
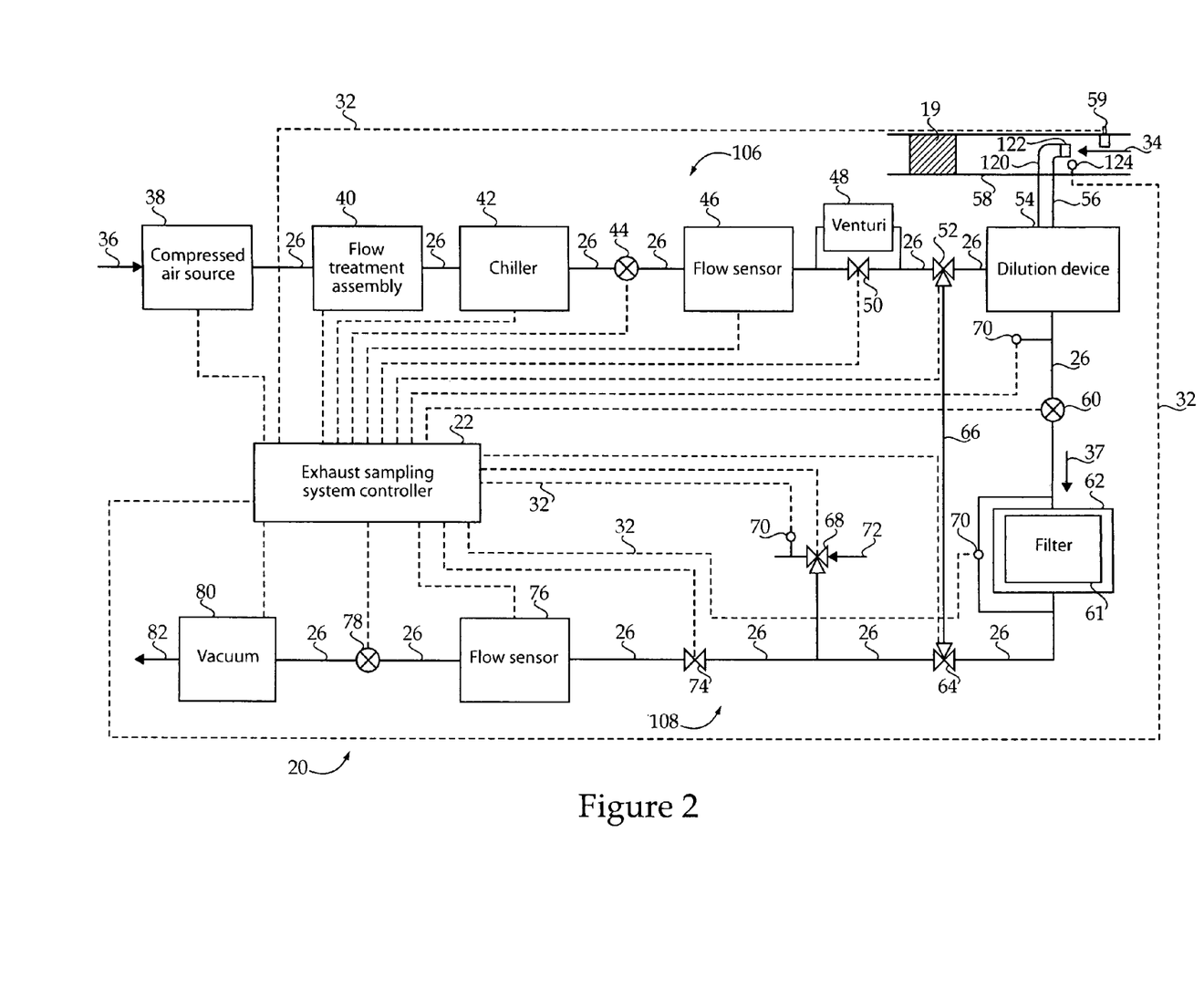
FIG. 2 is a diagrammatic illustration of a sampling system according to an exemplary embodiment of the present disclosure.

Referring now to FIG. 2, an exhaust sampling system 20 in accordance with an exemplary embodiment of the present disclosure includes a dilute side 106 and a total side 108. A dilution device 54 of the dilute side 106 may be fluidly connected to the exhaust line 58 of the power source 10 (FIG. 1), and the dilute side 106 may further include, for example, a compressed air source 38, a flow treatment device 40, a chiller 42, a flow sensor 46, and a plurality of flow control and/or other types of valves. In addition, the dilution device 54 of the dilute side 106 may be fluidly connected to a filter 62 of the total side 108, and the total side 108 may further include, for example, a flow sensor 76, a vacuum 80, and a plurality of flow control and/or other types of valves. The exhaust sampling system controller 22 and/or the test cell controller 24 (FIG. 1) may be electrically connected to one or more of the components of the exhaust sampling system 20. It is understood that each of the dash lines illustrated in FIG. 2 are control lines 32 and each of the solid lines connecting the components of the exhaust sampling system 20 illustrated in FIG. 2 are flow lines 26.

As will be described in greater detail below, the components of the dilute side 106 may be configured to compress, treat, cool, measure, and/or regulate a dilute flow 36 of ambient air. The dilute flow 36 may be combined with a flow of exhaust gas that is extracted from the exhaust flow of the power source 10. In addition, the flow rate of the dilute flow 36 may be rapidly adjusted by the dilute side components in response to the sensed difference between the flow rate of the dilute flow 36 and the flow rate of the combined (dilute and extracted) flow.

The compressed air source 38 may include, for example, an air compressor or any other device capable of compressing a gas and delivering the compressed gas through the flow lines 26. For example, in one embodiment of the present disclosure the compressed air source 38 may be a shop air compressor of a type known in the art and may supply compressed air at approximately 70 to 110 psi. This range may be increased or decreased depending on the size of the compressed air source 38 used and the pressure or volume required by exhaust sampling system 20. The compressed air source 38 may be configured to deliver a substantially constant, substantially uniform flow of compressed air to the components of the exhaust sampling system 20. As illustrated in FIG. 2. A dilute flow 36 may enter an intake of the compressed air source 38 and may be compressed therein.

The compressed air source 38 may be fluidly connected to a flow treatment assembly 40 via a flow line 26. The flow lines 26 of the present disclosure may be any type of tubing, piping, or hose known in the art. The flow lines 26 may be, for example, plastic, rubber, aluminum, copper, steel, or any other material capable of delivering a compressed gas in a controlled manner, and may be flexible or rigid. The length of the flow lines 26 may be minimized to facilitate operation of the exhaust sampling system 22, while reducing the pressure drop between the components thereof. In an exemplary embodiment, component 26 may be fabricated from stainless steel tubing or PTFE-line hose.

The flow treatment assembly 40 may be any assembly and/or collection of components configured to filter, treat, and/or otherwise clean the dilute flow 36. In an exemplary embodiment, the flow treatment assembly 40 may include a charcoal scrubber, a dessecator and/or a particulate filter (not shown). It is understood that the components of the flow treatment assembly 40 may be separate devices disposed within a single housing. Alternatively, the components of the flow treatment assembly 40 may be disposed in separate housings. The charcoal scrubber of the flow treatment assembly 40 may be configured to remove, for example, hydrocarbons from the dilute flow 36. The dessecator of the flow treatment assembly 40 may be configured to remove, for example, water from the dilute flow 36, and the particulate filter may be an ultra fine particulate filter of a type known in the art. Such particulate filters may be configured to capture and/or remove impurities contained within the dilute flow 36, such as, for example, sluff from the dessecator, charcoal from the charcoal scrubber, and/or any other airborne impurities. The flow treatment assembly 40 may be connected to a chiller 42 via a flow line 26.

The chiller 42 may be any device or combination of devices configured to reduce the temperature of a flow fluid passing therethrough. The chiller 42 may be connected to, for example, a source of coolant to assist in reducing the temperature of the fluid flow passing therethrough. The chiller 42 may include, for example, a heat exchanger such as, for example, a radiator and/or any other conventional heat exchange device. In an exemplary embodiment of the present disclosure, the chiller 42 may be configured to reduce the temperature of the dilute flow 36 to approximately 20° C. The chiller 42 may be fluidly connected to a flow sensor 46 via a flow line 26, and an isolation valve 44 may be disposed within the flow line 26 between the chiller 42 and the flow sensor 46. It is understood that in an exemplary embodiment, the compressed air source 38, the flow treatment assembly 40, and/or the chiller 42 may be independently controllable and, thus, may not be electrically connected to the exhaust sampling system controller 22.

The isolation valve 44 may be any type of controllable fluid valve known in the art such as, for example, a poppet valve, a butterfly valve, or a ball valve. The isolation valve 44 may be controlled to completely restrict a flow of air from passing therethrough or may allow the flow to pass unrestricted. In an exemplary embodiment, the isolation valve 44 may be a ball valve configured to substantially fully open and/or substantially fully close fluid communication between, for example, the chiller 42 and the flow sensor 46. The isolation valve 44 may be controlled by any conventional pneumatic and/or electric actuator such as, for example, a solenoid.

The flow sensor 46 may be any device and/or collection of devices configured to sense the volumetric flow rate and/or other characteristics of a flow passing therethrough. In an exemplary embodiment, the flow sensor 46 may include a laminar flow element configured to measure the volumetric flow rate of the dilute flow 36. The laminar flow element may include, for example, a matrix of small tubes in, for example, a honeycomb arrangement, and the laminar flow element may be any conventional type of laminar flow element known in the art.

In addition to the laminar flow element discussed above, the flow sensor 46 may further include one or more components configured to sense, for example, the pressure and/or temperature of the dilute flow 36 passing through the flow sensor 46. Such pressure and/or temperature measurements may be used to derive the density of the dilute flow 36. Thus, the exhaust sampling system controller 22 may use the volumetric output of the laminar flow element in conjunction with the density output of these additional components to determine, for example, the mass flow rate of the dilute flow 36.

The additional components of the flow sensor 46 may include, for example, a pressure differential transducer, an absolute pressure transducer, and a platinum resistance thermistor. Although these additional elements are not shown in FIG. 2 it is understood that the pressure differential transducer may include one or more pressure sensors disposed upstream and/or downstream of the laminar flow element and configured to measure a pressure drop across the laminar flow element. The absolute pressure transducer may be disposed upstream of the laminar flow element and may be configured to measure the absolute pressure of, for example, the dilute flow 36. In addition the platinum resistance thermistor may be disposed immediately upstream of an inlet of the laminar flow element and may be configured to sense the temperature of the dilute flow 36 entering the laminar flow element. The platinum resistance thermistor may be inherently stable due to the platinum and/or other metals utilized within the thermistor, and may be configured to make relatively fine and/or accurate temperature measurements.

The flow sensor 46 may be fluidly connected to the dilution device via a flow line 26, and a flow control valve 50 may be disposed in the flow line 26. The flow control valve 50 may be any type of controllable fluid valve known in the art configured to regulate a pressurized flow of fluid. The flow control valve 50 may be configured to rapidly respond to control signals sent from, for example, the exhaust sampling system controller 22.

The flow control valve 50 may be, for example, an electromagnetic valve having a plunger maintained in a magnetic field such that the mechanical resistance placed on the plunger is substantially zero while the flow control valve 50 is in use. The flow control valve 50 may be, thus, substantially instantly variable. The flow control valve 50 may have a response time of less than or equal to 75 milliseconds and may be configured to receive and react to substantially continuous flow commands sent by the exhaust sampling system controller 22. The flow control valve 50 may be configured to adjust the flow rate of the dilute flow 36 and/or the extracted flow according to the flow commands. The flow commands may be in response to, for example, the volumetric and/or mass difference between a combined flow 37 and the dilute flow 36.

The flow control valve 50 may also be configured to control the proportionality of the exhaust flow sample that is extracted from the exhaust flow of the power source 10 (FIG. 1). As used herein, the term "proportionality" is defined as the amount of exhaust flow that is extracted relative to the total exhaust flow 34 produced by the power source 10 at the time of the extraction.

In an exemplary embodiment of the present disclosure the exhaust sampling system 20 may further include a venturi 48. The venturi 48 may be, for example, a critical flow of venturi and/or any other type of venturi known in the art. As illustrated in FIG. 2, an inlet of the venturi 48 may be fluidly connected downstream of an outlet of the flow sensor 46 and upstream of an inlet of the flow control valve 50. An outlet of the venturi 48 may also be connected to the flow line 26 downstream of an outlet of the flow control valve 50 and upstream of a valve 52. In an exemplary embodiment the venturi 48 may be sized and/or otherwise configured to receive approximately 80% of the maximum flow passing through a dilute side 106 of the exhaust sampling system 20. In such an embodiment the remaining 20% of the maximum flow traveling through the dilute side 106 may be controlled by the flow control valve 50. The venturi 48 may be configured to sense, for example, the flow rate and/or other characteristics of the dilute flow 36 passing through the dilute side 106 of the exhaust sampling system 20. The venturi 48 may be electrically connected to, for example, the exhaust sampling system controller 22 and may be configured to transmit, for example, sensed flow information thereto. It is understood that, in other exemplary embodiments of the present disclosure, the venturi 48 may be omitted. In such embodiments, the flow control valve 50 may be a single point of flow control.

An outlet of the flow control valve 50 may be fluidly connected to an inlet of the valve 52 via a flow line 26. The valve 52 may be a standard two-way valve, three-way valve, or any other type of controllable flow valve known in the art. In an exemplary embodiment, the valve 52 may be configured to direct the dilute flow 36 to pass from the dilute side 106 to a total side 108 of the exhaust sampling system 20 via a bypass line 66. In addition, the valve 52 may be configured to transmit the dilute flow 36 to an inlet of a dilution device 54 while substantially completely preventing flow from the dilute side 106 through the bypass line 66. In an exemplary embodiment, flow line 26 may contain a heat exchanger (not shown) downstream of valve 52 and upstream of dilution device 54 to further control the temperature of dilution air entering dilution device 54.

As discussed above, an extraction component or test probe 56 of the dilution device 54 may be disposed within and/or fluidly connected to an exhaust line 58. In the illustrated embodiment, the test probe 56 is positioned in exhaust line 58 upstream from a particulate filter 19 in order to test particulate matter production of the engine while the presence of the particulate trap 19 produces accurate back pressure conditions in exhaust line 58 corresponding to those that might be encountered in the field. As an alternative, the particulate trap 19 could be replaced with some valve, such as a butterfly type valve that would mimic the back pressure behavior of a particulate trap in the exhaust line 58 without departing from the present disclosure. The extraction component 56 may be configured to extract at least a portion of the exhaust flow 34 of the power source 10 during operation. The extraction component 56 may be fluidly connected to the dilution device 54 such that the extracted portion of the exhaust flow 34 may be delivered to the dilution device 54 through the extraction component 56. In the case of the exhaust sampling system 20 illustrated in FIG. 2, the test probe 56 may include an elbow portion 120 that terminates in a tip 122 that includes a flow opening for capturing a portion of exhaust flow 34.

The filter 19 may be, for example, a particulate matter filter and/or any other type of exhaust flow filter known in the art. Such types of filters may include, for example, a foam cordierite sintered metal, or silicon carbide type filter. The filter 19 may include, for example, filter media, and the filter media may be made of any material useful in removing pollutants from a flow of gas passing therethrough. In an exemplary embodiment of the present disclosure, the filter media may contain catalyst materials capable of collecting, for example, soot, NOx, sulfur compounds, particulate matter, and/or other pollutants known in the art. Such catalyst materials may include, for example, alumina, platinum, rhodium, barium, cerium, and/or alkali metals, alkaline-earth metals, rare earth metals, or combinations thereof. The filter media may be situated horizontally, vertically, radially, or helically. The filter media may also be situated in a honeycomb, mesh, or any other configuration so as to maximize the surface area available for trapping, collecting, filtering, and/or removing pollutants.

The dilution device 54 may be a flow tunnel and/or other type of dilution device known in the art. For example, the dilution device 54 may include an air distribution tube and a central axis (not shown). The air distribution tube may be an elongate cylindrical tube of, for example, stainless steel or other like materials. The cylindrical tube may include a plurality of distribution holes formed in a central region of the cylindrical tube. The dilution device 54 may also include a housing forming an annular chamber peripherally about the central region of the cylindrical tube. The dilution device 54 may further include a center tube means for defining a second annular chamber within the cylindrical tube along the central axis. In an exemplary embodiment, the center tube means may be formed of sintered stainless steel, or other like materials, and the porous center tube may include a plurality of relatively small pores opening inwardly into an internal passage.

The dilution device 54 may be configured to receive the dilute flow 36 and may combine the dilute flow 36 with the extracted portion of the exhaust flow 34 discussed above, thereby diluting the extracted portion. An outlet of the dilution device may be fluidly connected to an inlet of the filter holder 62 via a flow line 26, and a valve 60 may be disposed in the flow line 26 between the dilution device 54 and the filter 61. The valve 60 may be, for example, an on/off valve, and the valve 60 may be mechanically similar to, for example, the isolation valve 44 discussed above. The valve 60 may be configured to substantially completely open or substantially completely close fluid communication between the dilution device 54 and the filter holder 62.

The filter holder assembly 62 may be, for example, a pressure and/or vacuum resistance-sealed device recognized in the art for the containment of filter media 61 for the purpose of gravimetric sampling of aerosol sampling of gaseous streams. An exemplary version of this device is a stainless steel version, such as described in 40 CFR part 86.1310-2007, ISO 8178-1, and others. The filter media 61 contained in filter holder 62 may be, for example, sampling media of specific retention quality defined in regulatory text for gravimetric characterization of emitted particulate mass. The size, media and usage of this type of filter may be specifically defined in regulatory text, but are generally highly engineered for aerosol sampling of gaseous streams. Such types of filter media 61 may include but are not limited to membrane filters, fiber media filters with PTFE coating for resistance to aqueous uptake, quarts fiber media and others.

In an exemplary embodiment of the present disclosure, one or more diagnostic or measurement devices 70 may be disposed proximate an inlet and/or an outlet of, for example the dilution device 54, the filter 61, and/or other components of the exhaust sampling system 20. The diagnostic devices 70 may be, for example, internal to or external from the components of the exhaust sampling system 20, and may be, for example, fluidly connected to one or more of the flow lines 26 of the exhaust sampling system 20. The diagnostic devices 70 may be any sensing devices known in the art such as, for example, flow meters, emission meters, particle size sensors, pressure transducers, radio devices, or other sensing and/or sampling devices configured to sense engine emissions. Such diagnostic devices 70 may sense, for example, soot and/or NOx level, temperature, pressure, and/or other flow characteristics. Each of the diagnostic devices 70 may be electrically connected to the exhaust sampling system controller 22 and may be configured to send sensed information to the exhaust sampling system controller 22 via control lines 32. As shown in FIG. 2, in an exemplary embodiment, the diagnostic device 70 associated with the filter 61 may be, for example, a differential pressure transducer configured to sense the pressure drop across the filter 61. Such an exemplary diagnostic device may be fluidly connected proximate an inlet of the filter 61 and proximate an outlet of the filter 61.

In an exemplary embodiment of the present disclosure, the exhaust sampling system 20 may further include a thermistor 59. The thermistor 59 may be, for example, a resistor, a temperature sensitive semi-conductor, and/or any other type of temperature sensor known in the art. The thermistor 59 may be, for example, a fast response thermistor, and may include materials or components whose resistance changes rapidly when exposed to a change in temperature. As illustrated in FIG. 2, a component of the thermistor 59 may be fluidly connected to the exhaust line 58 and the thermistor 59 may be configured to sense changes in temperature of the exhaust flow 34 passing therethrough. The thermistor 59 may be electrically connected to, for example, the exhaust sampling system controller 22 and may be configured to transmit, for example, sensed temperature, flow, and/or other information thereto. It is understood that, in other exemplary embodiments of the present disclosure, the thermistor 59 may be omitted. In addition to thermistor 59, the sampling system 20 may include a pressure sensor 124 for determining the absolute pressure in the exhaust flow 34 at the location of test probe 56. Pressure sensor 124 may be useful in tracking a pressure increase and a magnitude of maximum pressure that occurs at the test probe location during a transient, such as when the power source (engine) is undergoing an acceleration. Those skilled in the art will appreciate that the presence of particulate filter 19 creates back pressure on power source 10, and that back pressure may increase and peak during a transient operating condition.

The dilute side 106 of the exhaust sampling system 20 may be connected to the total side 108 via a bypass line 66 fluidly connecting the valve 52 to a valve 64. An outlet of the filter holder 62 may also be connected to the valve 64 via a control line 26. Accordingly, during use a dilute flow 36 may be directed through the valve 52 to valve 64, via the bypass line 66, thereby bypassing, for example, the dilution device 54 and the filter 61. Alternatively, the dilute flow 36 may be directed through valve 52 to the dilution device 54 and the filter holder 62 before passing through the valve 64, and the valve 52 may prohibit flow from passing from the dilute side through the bypass line 66. As discussed above with respect to valve 52, the valve 64 may be, for example, a two-way valve, a three-way valve, or any other type of controllable flow valve known in the art. The valve 64 may be sized and/or otherwise configured to allow any range of flow to pass from the filter 61 to downstream components on the total side 108 of the exhaust sampling system 20. Accordingly, the valve 64 may be sized to handle larger flow volumes (i.e. combined flows) than the valve 52. An outlet of the valve 64 may be fluidly connected to an inlet of a flow control valve 74 via a flow line 26.

The flow control valve 74 may be structurally similar to the flow control valve 50 discussed above with respect to the dilute side 106 of the exhaust sampling system 20. As illustrated in FIG. 2 a flow line 27 may be fluidly connected between valve 64 and flow control valve 74. A valve 68 may be fluidly connected to the flow line 27 and configured to receive at least a portion of the flow exiting an outlet of the valve 64. The valve 68 may be any two-way or three-way valve known in the art. The valve 68 may be configured to allow a flow of ambient air 72 to pass through the flow line 27 to the flow control valve 74. Alternatively the valve 68 may be configured to receive a portion of the flow exiting valve 64 for sensing. A diagnostic device 70 may be fluidly connected to an outlet of the valve 68 to assist in sensing the flow received from valve 64.

In an exemplary embodiment, the diagnostic device 70 fluidly connected to the outlet of the valve 68 may be, for example, a flow meter sized to measure a flow through the valve 68. The flow through the valve 68 may be, for example, volumetrically analogous to the flow through the extraction component 56. In such an exemplary embodiment, valve 52 and valve 64 may be controlled to direct a dilute flow 36 to valve 68, therefore bypassing the dilution device 54 and the filter 62. For example, during an quality control check, the flow sensor 76, the flow control valve 74, the flow sensor 46, the venturi 48, and the flow control valve 50 may be placed in series, and a flow potential may be created by the vacuum 80 and the compressed air source 38. In addition, during the exemplary quality control check, the flow through the flow sensor 46 may be set to, for example, 85 liters per minute and the flow through a flow sensor 76 may be set to, for example, 100 liters per minute. The difference between these two flows may be a flow of ambient air drawn through the valve 68 (represented by flow arrow 72). The volume of the flow of ambient air may be substantially the same as the flow of exhaust gas that would be extracted by the extraction component 56 if the exhaust sampling system 20 was sampling exhaust gas. It is understood, however, that at any given time during operation, the flow through the extraction component 56 cannot be simultaneously identical to the flow through diagnostic device 70 proximate the valve 68.

It is understood that directly measuring the volume and/or other characteristics of the flow extracted from the power source exhaust flow by the extraction component 56 may be difficult. For example, directly measuring the amount of flow extracted from the exhaust flow may quickly contaminate any flow meter, or other device used to measure the flow directly, with particulate matter. In addition, the extracted flow may have a temperature in excess of 600° C. and thus conventional flow meters may not be suitable for measuring such high temperature flows. Accordingly, due to the difficulties associated with measuring the extracted flow with an inline flow meter, a pre-test or post-test assessment of the quality of the inferred extracted flow valve with a diagnostic device 70 as described above may be helpful.

An outlet of the flow control valve 74 may be fluidly connected to a flow sensor 76 via a flow line 26. The flow sensor 76 may be configured to measure, for example, the pressure, volume, mass, and/or other characteristics of the flow passing through the total side 108 of the exhaust sampling system 20. The flow sensor 76 may be any type of flow sensor known in the art In an exemplary embodiment, the flow sensor 76 may be a volumetric device similar to the flow sensor 46 discussed above with respect to the dilute side 106. Thus, the flow sensor 76 may include a laminar flow element and a number of additional components configured to assist in calculating the mass flow passing through the flow sensor 76. Such components may include, for example, a platinum resistance thermistor and an absolute pressure transducer. It is understood that while a pressure transducer configured to measure pressure drop may be associated with the laminar flow element of the flow sensor 46, in an exemplary embodiment of the present disclosure, a corresponding pressure transducer may not be required to sense and/or measure the pressure drop across, for example, the flow sensor 76. In addition, as discussed above with respect to the flow sensor 46 the components of the flow sensor 76 may be configured to assist in defining the density of the flow passing through the flow sensor 76. Accordingly, the flow sensor 76 may configured to measure the mass of the flow passing therethrough.

In an exemplary embodiment, the flow sensor 76 may include a positive displacement type flow meter. Such a flow meter may include, for example, one or more sets of lobes disposed on meshed gears (not shown). Such gears may be constructed of, for example, aluminum, stainless steel, platinum, and/or any other like metals, and may be very finely machined so as to reduce friction and/or resistance between each other when meshing. In an exemplary embodiment, as flow is directed through the flow sensor 76, the internal lobes and/or gears may be moved and/or turned by the flow in direct proportion to the amount of flow being directed through the flow sensor 76.

An outlet of the flow sensor 76 may be fluidly connected to a valve 78 via a flow line 26. The valve 78 may be structurally similar to the isolation valve 44 discussed above with respect to the dilute side 106. Accordingly the valve 78 may be configured to substantially open and/or substantially close fluid communication between the flow sensor 76 and the vacuum 80 of the exhaust sampling system 20. The vacuum 80 may be any conventional source of negative pressure known in the art. The vacuum 80 may include, for example a shop vacuum, a vacuum pump, and/or any other device capable of creating negative pressure. The vacuum 80 may be of any power or capacity useful in drawing flow through an exhaust sampling system such as the exhaust sampling 20 illustrated in FIG. 2. In an exemplary embodiment of the present disclosure, the vacuum 80 may be configured to have a low pressure spike signature. Such a vacuum 80 may be configured to direct a substantially constant negative pressure to components of the exhaust sampling system 20.

In general, in prior art testing using a sampling system 20 and a prior art test probe 56, the flow opening into the test probe is unrestricted as expected during steady state testing. Exhaust line 58 and sampling system 20 are preferably operated at atmospheric pressure (100 KPa) during steady state or transient testing, as the sampling location is downstream of the appreciable back pressure inducing devices, such as filters, valves, mufflers or catalysts. More recently, when developing engines intended to meet regulations requiring testing during transient engine operating episodes, such as an acceleration and deceleration, the exhaust stack pressure in the vicinity of test probe 56 will vary significantly due to back pressure inducement effects created by particulate filter 19, which can lead to oversampling and inaccurate results when determining engine out particulate matter production for the transient event. The oversampling may have several contributing factors that may all be traced back to the pressure increase, but may distort the testing procedure in different ways. For instance, the pressure rise at the test probe location itself may lead to increased mass flow through an unrestricted opening in a test probe 56. In addition, particulate matter concentrations may greatly increase during a transient event, which can compound the oversampling problem attributable to an increased mass flow into the sampling system 20. Finally, the increased pressure can also lead to a decrease in the mean free path between molecules which can lead to the formation of additional particulate matter in the exhaust line, and maybe even in the sampling system 20 due to the pressure increase, further distorting an accurate assessment of particulate matter production by the power source 10 during a transient event.

In order to achieve more accurate testing results during a transient event, the present disclosure contemplates the inclusion of a properly sized flow opening into the sampling system 20 that behaves in an essentially unrestricted manner during proportional sampling when steady state engine operating exist, but behaves as an orifice, or restricted flow opening, when pressure increases during the transient event. The result of this strategy causes a flow restriction when pressure increases resulting in less volumetric flow into the sampling system 20 at precisely the time when pressures might otherwise cause increased mass flow and precisely at the time when particulate matter concentrations are higher. As a result, sampling proportionality is maintained at proper rates and is not influenced by exhaust pressure peturbances brought about by increasing volumetric flow through the exhaust system. In addition, this strategy can also address the issue of particulate matter formation through changes in the molecular mean free path length within the sampling system 20 by the flow restriction resulting in lower pressures within the sampling system 20 that are less than exhaust stack pressures in the vicinity of the test probe location. This will result in a smaller decrease in the mean free path between molecules within the sampling system 20, hence leading to less spontaneous formation of nuclei mode particulate through heterogeneous or homogenous nucleation during sampling and dilution conditions that are substantially inconsistent with atmospheric due to this pressure induced decrease in mean free path within the sampling system 20 itself during transient tests. Further, the rates of coagulation and agglomeration are comparatively mature, however the spontaneous formation and/or growth of smaller particulate is effected by mean free path length. Hence, mitigation of the artificially high pressure condition within the sampling system 20 during transient testing may result in improved analysis of particle sized distribution using separate devices extracting flow prior to filter holder 60 from system 20.

In order to effectively carry out this strategy and reduce oversampling during transient events, the present disclosure also includes a strategy for arriving at a flow opening sizing for the test probe 56 that can lead to more accurate results during a specific transient test of a specific power source 10. In particular, the present disclosure includes a strategy for tuning the flow opening size into test probe 56 to suit the specific pressure increase signature associated with a specific transient event while also taking into account the desired volumetric flow rate of exhaust into sampling system 20 such as during steady state conditions.

Figure 3:
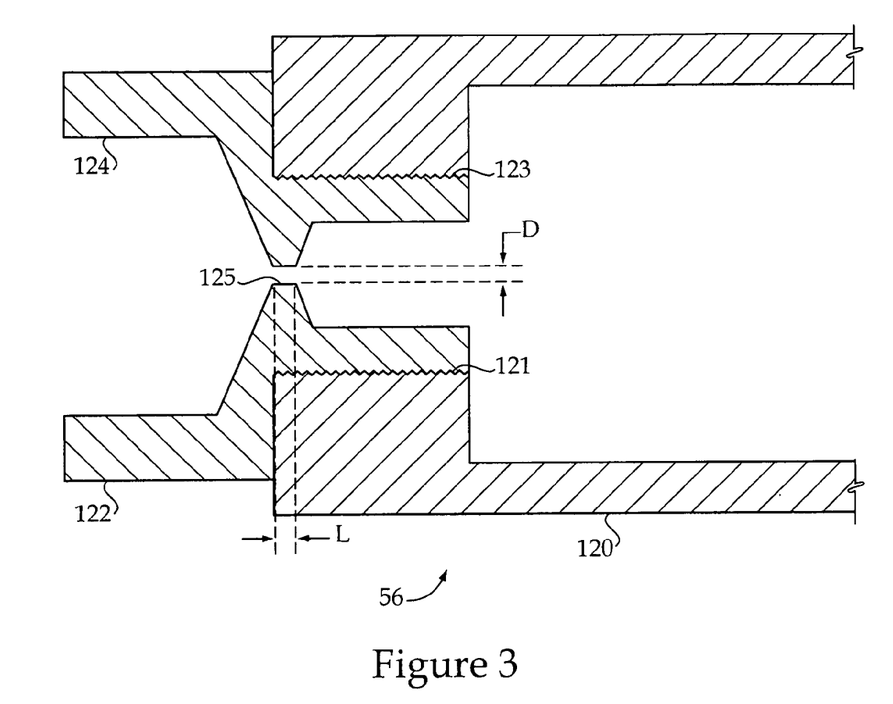
FIG. 3 is an enlarged sectioned view of the tip region of test probe 56.
Figure 4:
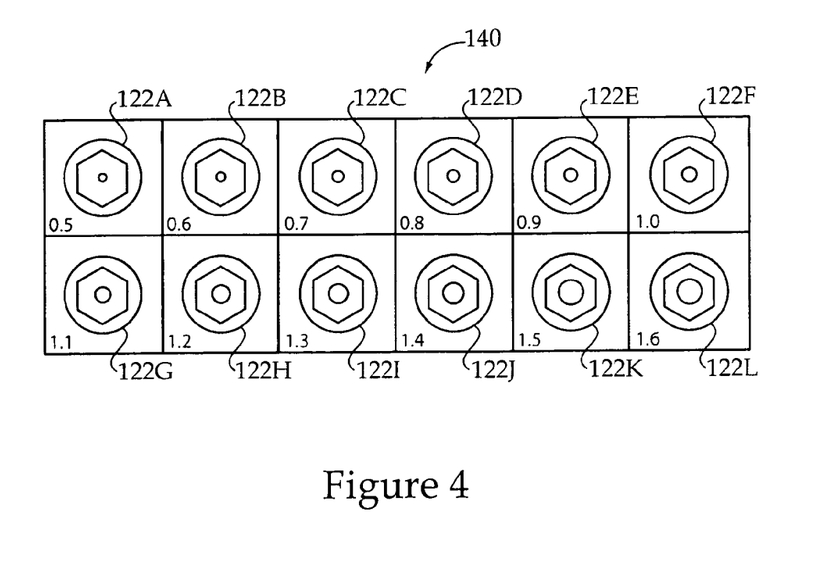
FIG. 4 is a schematic view of a kit that includes a plurality of tips having different sized flow openings.

Referring to FIG. 3, the end portion of a test probe 56 according to the present disclosure is shown as including an elbow section 120 and an attached tip 122 that defines a flow opening 125 that has a length L and a diameter D. Although tip 122 may be permanently attached to elbow section 120, such as via a weld or otherwise, in the illustrated embodiment, the tip 122 includes a set of external threads 123 that mate with a set of internal threads 121 included on the end of elbow section 120. Attachment is facilitated by including, for example, a tool interface 124, which in the illustrated embodiment takes a form of a hex head opening for threading different tips 122 having different sized flow openings 125 to elbow section 120. Tool interface 124 could be eliminated or take another form. In a preferred version of the disclosure, the L/D ratio for the flow opening 125 is such that it behaves as an orifice rather than exhibiting capillary type behavior. Thus, in terms of the present disclosure, an orifice means a flow opening with a relatively small L/D ratio that creates a flow restriction when a pressure differential across the flow opening 125 is at certain levels, such as those associated with a specific transient being tested. Thus, the flow opening 125 can only fairly be characterized as an orifice when the pressure differential across the flow opening is relatively high. On the other hand, the present disclosure recognizes that the flow opening 125 should be relatively unrestricted to exhaust flow into sampling system 20 when a pressure differential across the flow opening 125 is relatively low, such as during steady state operating conditions of the power source 10. FIG. 4 is of interest for showing a kit 140 of different tips 122A-L each having different sized flow openings, with one of the tips 122A-L being appropriate to improve accuracy for testing transients having a specific pressure increase signature as well as a desired volumetric flow rate into sampling system 20. Thus, for testing a different transient condition, possibly for a different power source 10, one might detach tip 122 and replace it with a different tip 122A-L from kit 140 that relates to the specifies of the new transient being tested.

Although the disclosure has been illustrated in the context of a flow opening with a relatively small L/D ratio to produce an orifice effect at higher pressure differentials across the opening, the present disclosure also contemplates alternative capillary type flow openings that have a relatively large L/D ratio that effectively causes the flow opening to be more restrictive at higher pressure differentials across the flow, but relatively unrestricted when flow pressure differentials are relatively low, such as at steady state operating conditions. Although this alternative is contemplated and falls within the scope of the present disclosure, the increased complexity of flow in capillary tube like passageways is generally more complex than flow restrictive behavior in flow orifices with a relatively small L/D ratio as discussed above. Nevertheless, the disclosure could be practiced with either strategy for producing the unrestricted and restricted flow characteristics at the right pressure differentials for a specific transient of a specific power source.

Figure 5:
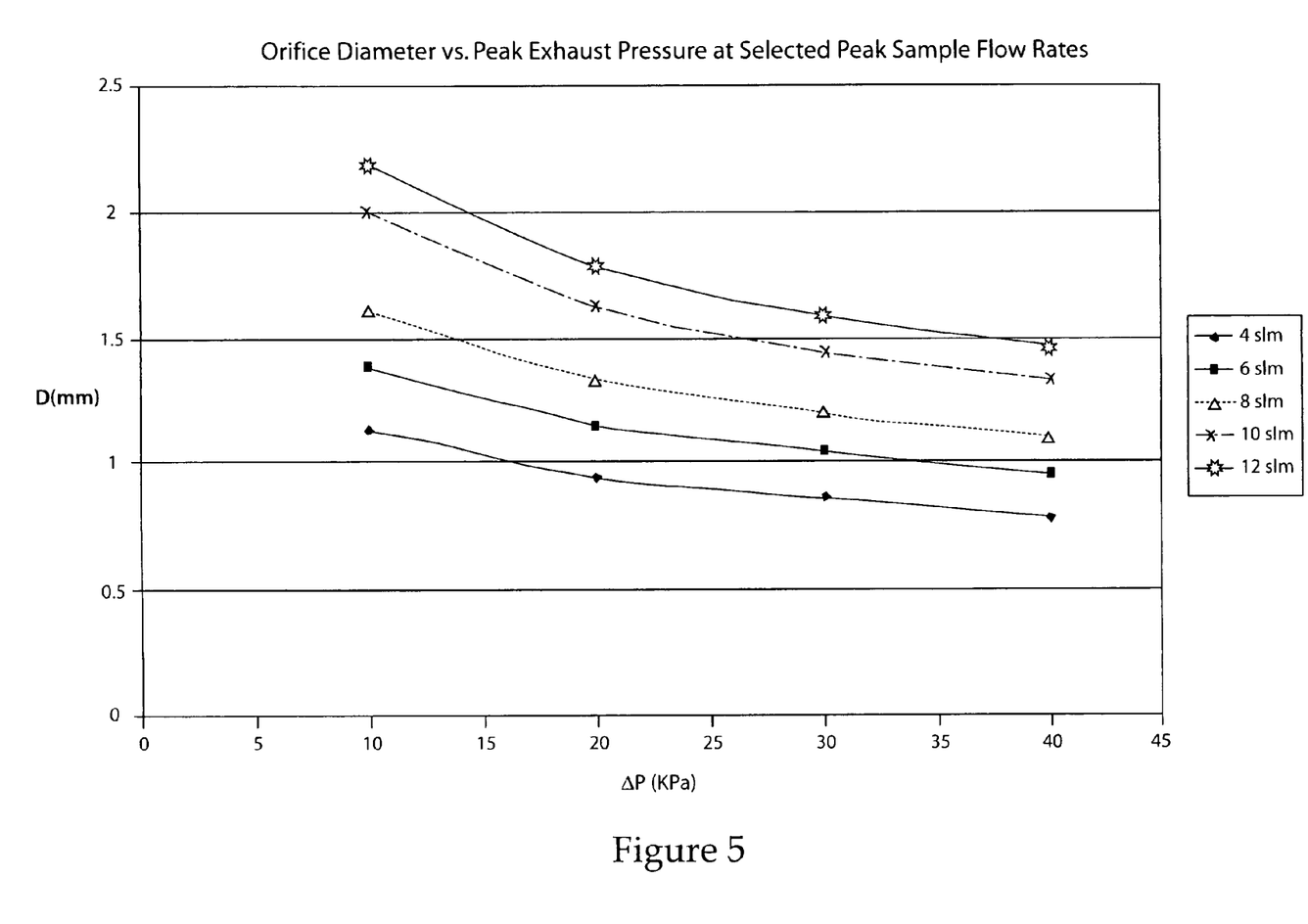
FIG. 5 is a graph of flow opening diameter size verses a pressure differential for several different volumetric flow rates into the sampling system.

Referring now to FIG. 5, an example graph showing how to choose the specific flow area size 125 based upon the expected pressure differential at the test probe location as well as the desired volumetric flow rate of exhaust into sampling system 20. The graph shows different curves for desired flow rates of four liters per minute, six liters per minute, eight liters per minute ten liters per minute and twelve liters per minute. The designation "slm" refers to these volumetric flow rates that have been standardized for temperature and pressure in a known manner. The bottom axis shows the expected maximum pressure differential at the test probe location 56 between the absolute pressure in the exhaust stack and atmospheric pressure (100 KPa). This number can be determined for a specific transient by sensing pressure during a transient with particulate filter 19 in place prior to actually performing the testing procedure according to the present disclosure. The left side axis shows what flow opening diameter size (D) will lead to improved results over a prior art test probe that remains unrestricted throughout a transient event. FIG. 5 assumes a flow opening with a circular cross section corresponding to a flow area of $\pi D^2/4$, but the disclosure also contemplates non-circular flow openings with a corresponding flow area. In one specific example, if the expected pressure differential was about 40 KPa at a desired volumetric flow rate of ten liters per minute, the flow opening diameter size ought to be about 1.3 millimeters (flow area=1.3 mm$^2$), which may lead to selecting tip 1221 from kit 140.

Figure 6:
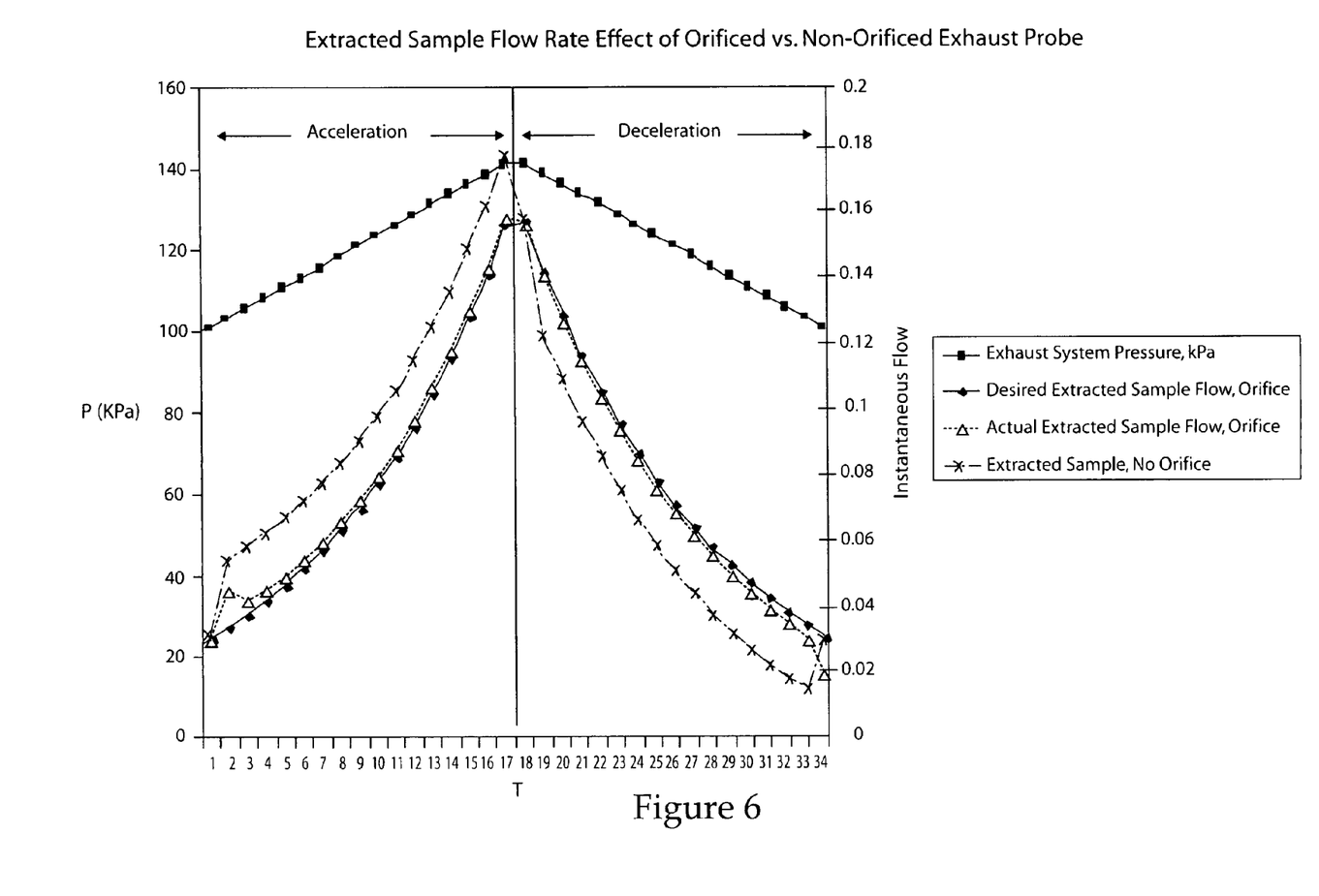
FIG. 6 shows a graph of a pressure signature during a transient condition along with a comparison of a desired extracted sample flow, an actual extracted sample flow using a prior art test probe, and an extracted sample flow with the inclusion of a tip 122 according to the present disclosure.
Figure 7:
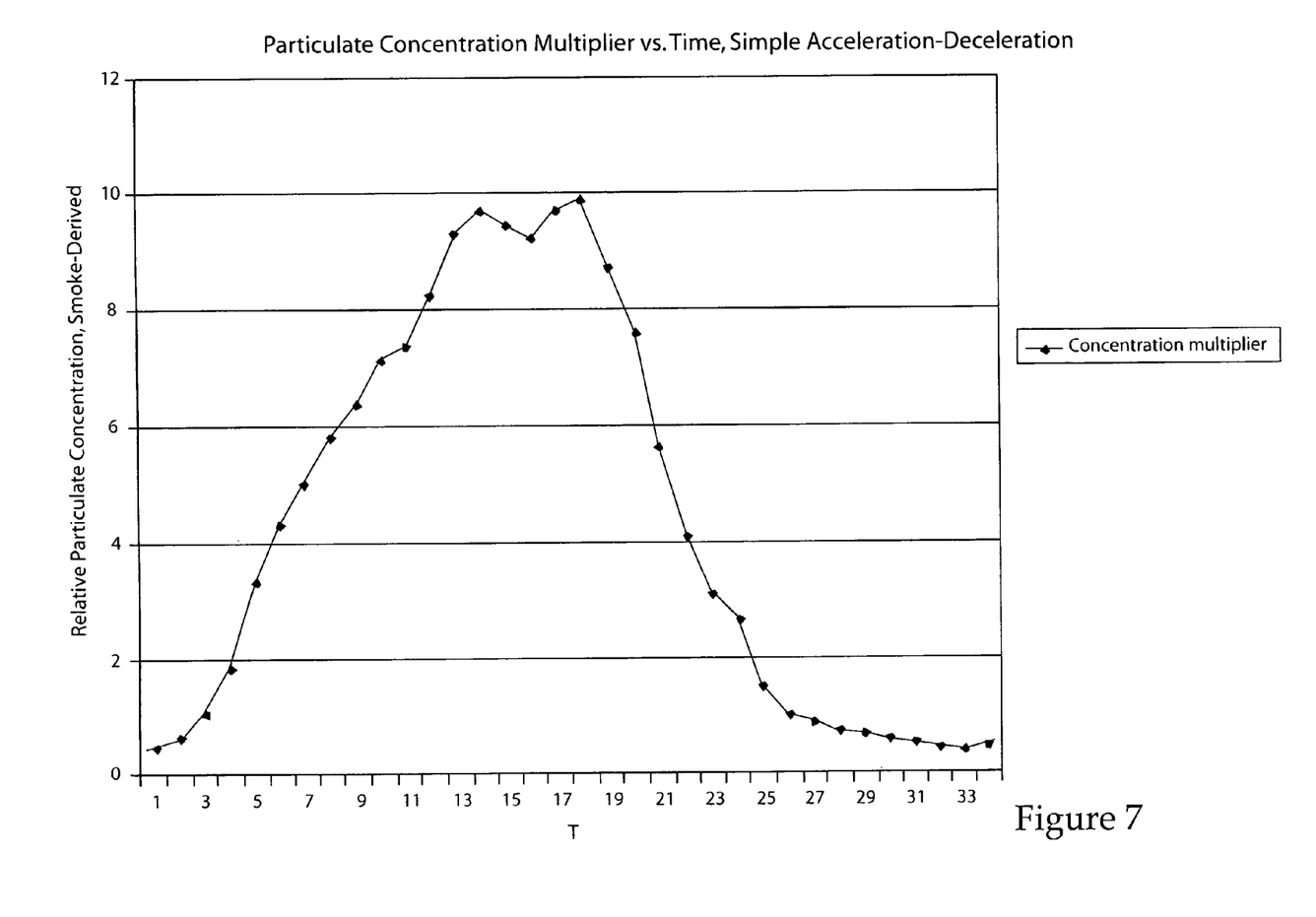
FIG. 7 is a graph showing particulate matter concentration verses time for the transient event illustrated in FIG. 6.
Figure 8:
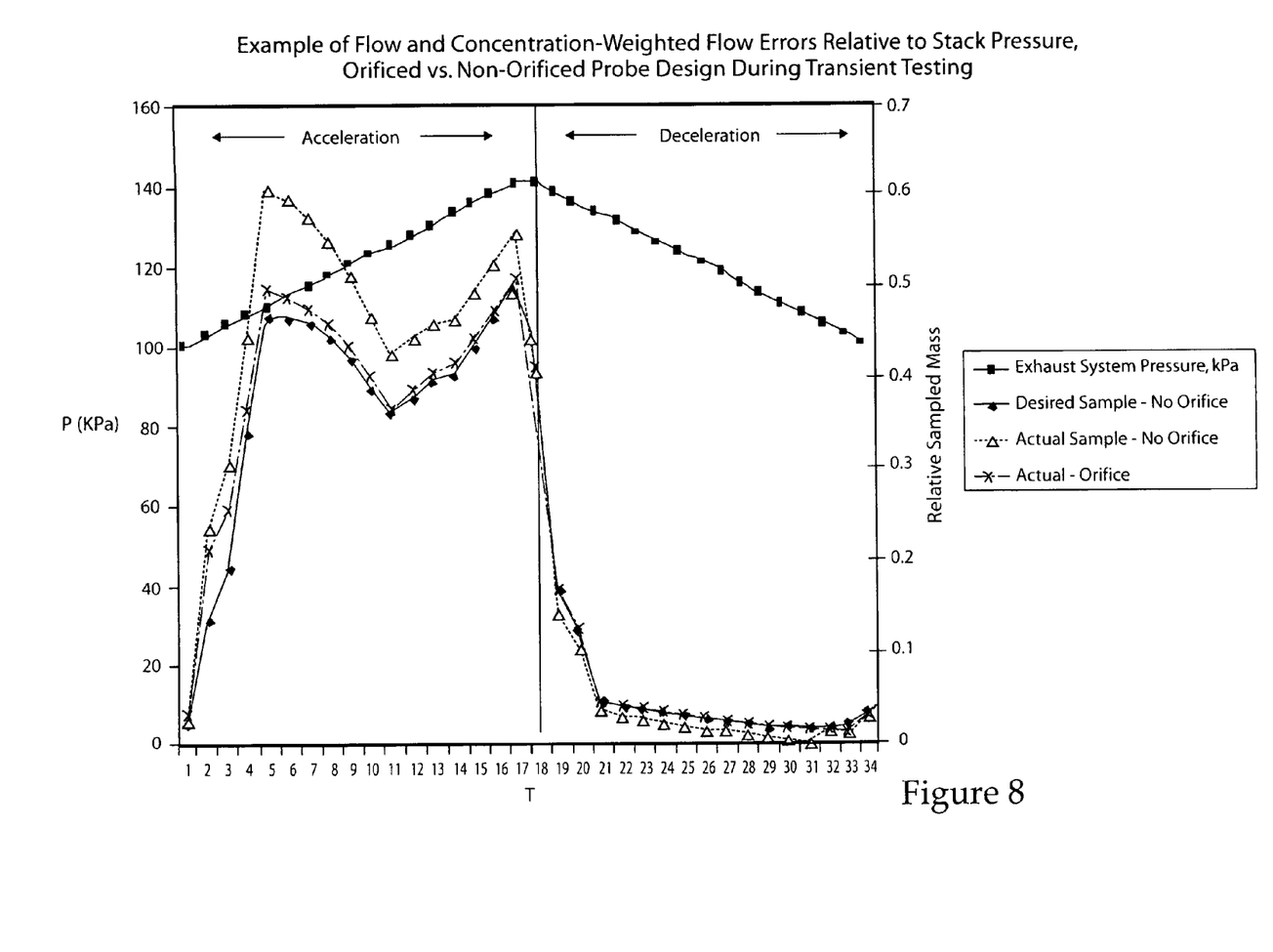
FIG. 8 is a graph similar to that of FIG. 6 except showing relative sampled mass taking account both the volumetric flow rate sampling of FIG. 6 combined with the particulate matter concentration increase reflected in FIG. 7 to show a comparison between desired mass sample, an actual mass sample according to the prior art, and an actual sample utilizing a tip according to the present disclosure.

Referring now to FIGS. 6, 7 and 8, the accuracy of sampling system 20 is shown for a specific transient in which the power source 10 accelerates and decelerates, which results in a pressure increase at the test probe location from 100 KPa to about 140 KPa and then back to 100 KPa during the transient. Thus 100 KPa represents a low pressure differential when flow into test probe 56 is unrestricted at a beginning of the transient, but 140 KPa represents a relatively high pressure differential when flow into test probe 56 is restricted during the transient being tested. Referring specifically to FIG. 6, this graph shows how the flow rate into sampling system 20 increases responsive to the pressure increase to result in an excess volumetric flow rate into the sampling system 20. Thus, the other three curves in FIG. 6 show a desired extracted sample flow rate, an actual extracted flow rate with the flow tip of FIG. 3 and an oversampling flow rate with no change in the flow opening of a prior art test probe. This graph shows that by the inclusion of the tip 122 with a specially tuned size flow opening 125, the actual extracted sample flow rate closely tracks that of the desired extracted sample flow rate. The graph of FIG. 7 is useful in illustrating that the particulate matter concentration increases greatly during the transient event and peaks somewhere in the vicinity of when the power source 10 transitions from acceleration to deceleration. This graph is useful in illustrating the fact that if oversampling of volumetric flow rate occurs, the problem is compounded by the fact that the particulate matter concentration is high during transient events. When the influences of both FIGS. 6 and 7 are combined, FIG. 8 shows a comparison of weighted sampling mass when taking into consideration adjustments for particulate matter concentration (FIG. 7) and volumetric flow rate into sampling system 20 as illustrated in FIG. 6. This graph is useful in showing that the actual sample according to the prior art without a specially sized flow opening 125 substantially exceeds the desired sample lending to inaccurate results. On the other hand, by including the flow opening 125 of the present disclosure, the actual sample with the tip 122 closely tracks that of the desired sample leading to a reduced error in assessing particulate matter production of power source 10 during a transient event.

INDUSTRIAL APPLICABILITY

The disclosed exhaust sampling system 20 may be used with any diesel, gasoline, natural gas, and/or other combustion engines, furnaces, or power sources known in the art. As discussed above, the exhaust sampling system 20 may be used for testing, design, development, and/or certification of such power sources. It is understood that such power sources may be used in conjunction with any machine, on-road vehicle, off-road vehicle, stationary machine, and/or other exhaust producing devices known in the art. The sampling system of the present disclosure is also applicable to testing various combustion sources during transient events by selecting a suitably sized tip 122 having a flow opening 125 that is tuned to take into consideration the desired volumetric flow rate into sampling system 20 along with taking into consideration the expected pressure increase signature associated with the transient event being tested. It is the desired volumetric flow rate that may be derived from regulation protocols that is associated with the graph of FIG. 5, when being used to select an appropriate tip 122A-L for a transient test.

Prior to performing the transient test, the pressure signature characteristics associated with the transient should be identified either through modeling or actually gathering pressure data in the exhaust flow 34 at the test probe location using pressure sensor 124 with particulate filter 19 in place. When this is done, that information combined with the desired volumetric flow rate into sampling system 20 can be used in conjunction with the graph of FIG. 5 to select an appropriate tip 122A-L for increasing accuracy during the transient test. Once an appropriate tip 122A-L is selected, it may be attached to the elbow section 120 of the test probe 56 prior to performing the test sampling during the specific transient event.

Figure 9:
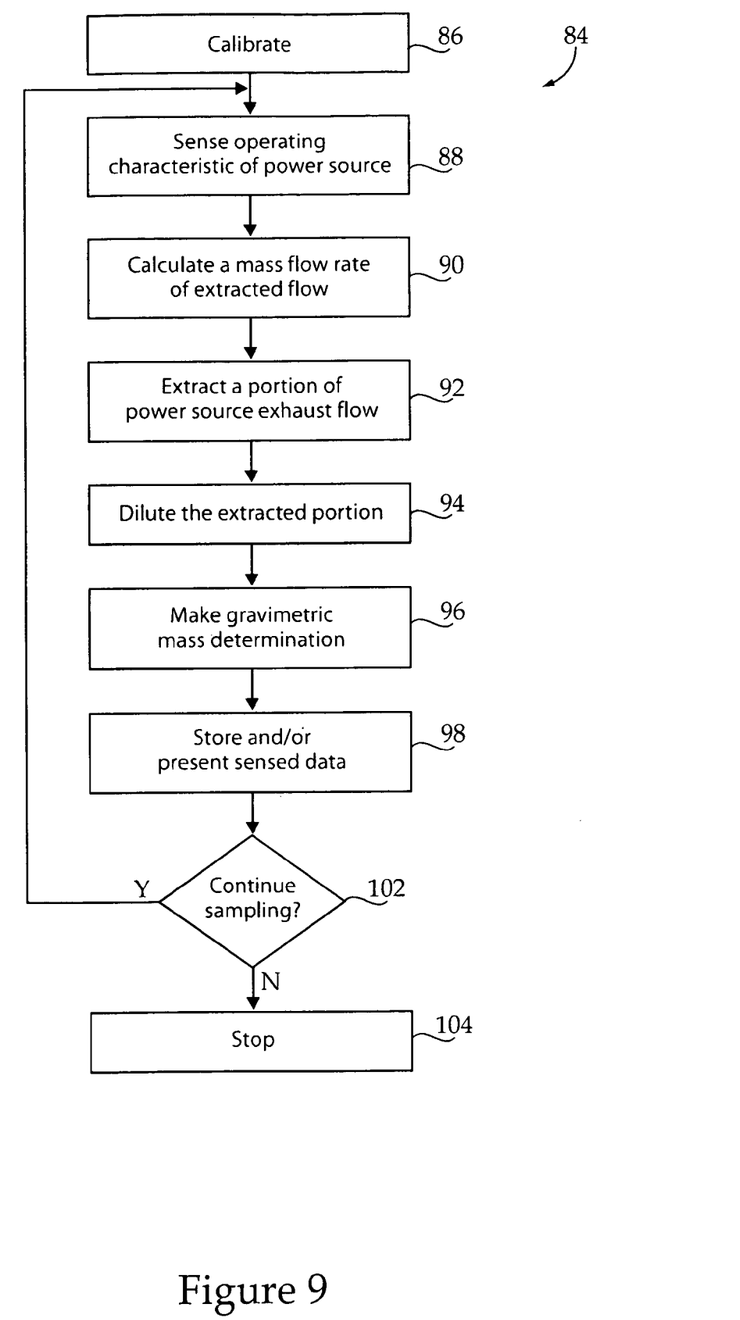
FIG. 9 is a flow chart of a sampling strategy according to an exemplary embodiment of the present disclosure.

A method for using the disclosed exhaust sampling system 20 to certify an exemplary power source will now be discussed with respect to the sampling strategy 84 illustrated in FIG. 9. It is understood that government regulations may require different testing scenarios depending upon the particular power source being certified. For example, some power sources may be certified under a steady state flow condition, while other power sources may be certified under transient flow conditions. As used herein, the term "transient flow condition" means flow conditions which are altered, modified, and/or otherwise changed during a test cycle. The exhaust sampling system 20 of the present disclosure may be used to certify power systems in both the transient and the steady state flow conditions. For the purposes of the present discussion, however, only a transient flow condition certification method will be discussed.

To begin using the exhaust sampling system 20 illustrated in FIG. 2, the user may bring the system 20 to thermal equilibrium. In thermal equilibrium, each component of the exhaust sampling system 20 may be at substantially the same temperature and, in an exemplary embodiment, the nominal temperature may be approximately 30 degrees Celsius. It is understood that, for example, the filter holder 62 and/or surrounding components must be maintained at a temperature of approximately 47 degrees Celsius (plus or minus, approximately, five degrees Celsius) for certification purposes. Once thermal equilibrium has been reached, the user may keep the system running at idle until sampling begins. In order to achieve thermal equilibrium, the user may, for example, set a desired combined flow rate and a desired dilute flow rate. The desired dilute flow rate may correspond to the volume of dilute flow 36 that is to be directed to the dilution device 54 via the flow control valve 50. The desired combined flow rate may correspond to the volume of the combined flow 37 that is to be directed to the filter 62 on the total side 108 of the exhaust sampling system 20.

While the system is being brought to thermal equilibrium, the dilute flow 36 may pass through the compressed air source 38, the flow treatment assembly 40, the chiller 42, the open isolation valve 44, the flow sensor 46, and the open flow control valve 50. The valve 52 may then direct the dilute flow 36 through the dilution device 54 and may substantially fluidly seal the bypass line 66. In addition, the valve 60 may be substantially closed, thus, the dilute flow 36 may be directed through the extraction component 56 to dislodge, for example, spurious particulate and/or other foreign matter that may have built up therein while the exhaust sampling system 20 was idle. The dilute flow 36 may then join the exhaust flow 34 and may be removed by the evacuation system 18 of the test cell 100. As illustrated in FIG. 2, a flow of gas 82 may be created by opening the valve 68 to allow a flow of ambient air to enter the valve 68, as illustrated by flow arrow 72. Alternatively, the operator can control the valves to extract a sample of the exhaust flow 34 and direct the sample through the filter 62. The operator may discard the filter media after extracting a sample during warm-up.

Once the exhaust sampling system 20 has reached thermal equilibrium, the user may calibrate the system (step 86). During calibration, the user may calibrate the dilute side 106 of the exhaust sampling system to the total side 108 in order to derive, for example, one or more polynomials for use in a control algorithm during sampling. In particular, during calibration the valve 44 and the flow control valve 50 may remain open and the valve 52 may direct the dilute flow 36 through the bypass line 66 to the valve 64. The dilute flow 36 may them pass to the flow control valve 74 and the valve 68 may be fully closed such that none of the dilute flow 36 may pass through flow line 27. In such a configuration, the flow sensor 46 may be put in series with the flow sensor 76. The exhaust sampling system 20 may be operated throughout a series of flow points specified by the user. By using the flow sensor 46, the flow sensor 76, and/or other components of the exhaust sampling system 20 to measure the dilute flow 36 at each of the flow points, the exhaust sampling system controller 22 may calculate a polynomial that represents the relationship between the flow sensor 46 and the flow sensor 76. This polynomial may be used to mathematically correct the flow measurements made by the flow sensor 46 to the flow measurements may by sensor 76 during operation of the exhaust sampling system 20.

After calibration, the operator may install a test filter media cartridge into the filter holder 62 and may control the engine to a first test point using the test cell controller 24. At the first test point, one or more diagnostic devices 70 of the exhaust sampling system 20 and/or the test cell 100 may sense one or more operating characteristics of the power source 10 (step 88). Such operating characteristics may include, for example, the flow of air to an intake of the power source 10, the rate of fuel consumption, power source temperature, and/or the mass flow rate of the exhaust flow 34. Based on the sensed operating characteristics described above, the exhaust sampling system controller 22 may calculate a desired mass flow of the extracted flow (step 90). The calculated desired mass flow of the extracted flow may correspond to the desired amount of exhaust flow to be extracted from the exhaust flow 34. In addition, the desired extracted mass flow may be substantially proportional to the mass flow of the exhaust flow 34.

The exhaust sampling system controller 22 may then control the components of the exhaust sampling system 20 to extract the calculated desired portion of the exhaust flow 34 (step 92). The exhaust sampling system controller 22 may also control the compressor 38 flow treatment assembly 40, chiller 42, flow sensor 46 and/or flow control valve 50 to direct a dilute flow 36 to the dilution device 54 in order to dilute the extracted portion of the power source exhaust flow (step 94). It is understood that, as used herein, the term "dilution" means mixing a flow of extracted exhaust with a flow of ambient air so as to simulate environmental conditions such as pressure and/or temperature. It is understood that during operation of the exhaust sampling system 20 the components of the exhaust sampling system 20 may operate at relatively high dilution ratios (i.e., the flow rate of the dilute flow 36 relative to the flow rate of the extracted flow may be relatively high). Such high dilution ratios may be required in order to reduce the temperature of the extracted flow to approximately 52° C. before the combined flow 37 reaches the filter 61.

During use, the exhaust sampling system 20 may substantially continuously and substantially instantly control the difference between the combined flow 37 and the dilute flow 36 with the flow control valves 74, 50 respectively. By controlling the difference between the flows 37, 36 in this way, the user may control, for example, the volume of the flow that is extracted from the exhaust flow 34 because the volume of the combined flow 37 is equal to the volume of the dilute flow 36 plus the volume of the extracted flow. Accordingly, by controlling the difference between the combined flow 37 and the dilute flow 36, the user may accurately control the proportionality of the extracted flow during a transient test cycle. Such a control strategy may be advantageous since it takes into account excursions in the exhaust flow 34 without directly sensing, for example, the mass flow rate and/or other characteristics of the exhaust flow 34 or the extracted flow. In addition, such a control strategy avoids the difficulties of directly measuring such flows discussed above.

The present disclosure contemplates a passive strategy for improving accuracy in particulate matter sampling during a transient event by choosing an appropriate flow opening 125 that acts in an unrestricted manner during steady state operating conditions preceding a transient event, but acts as an orifice or flow restriction when pressure increases during a transient event. Although the present disclosure has been illustrated in the context of restricting flow during pressure increases via usage of an appropriately sized orifice, those skilled in the art will appreciate that similar results could be achieved by geometry associated with capillary tube sizing to produce similar results. However, appropriately sizing a capillary tube may be more problematic than appropriate sizing of an orifice due to the increased complexity of flow properties in a capillary tube relative to the flow characteristics associated with predicting behavior of a simple orifice. In addition, although the present disclosure is illustrated in the context of positioning the flow opening in the tip 122 attached at the opening to the test probe 56, those skilled in the art will appreciate that the flow opening 125 could be located elsewhere in the sampling system without departing from the present disclosure. However, the specific sizing of the flow orifice being relocated to a different location in the sampling system 20 may require taking into account pressures at that location instead of at the test probe location as in the illustrated embodiment. While such an active control strategy may conceivably allow sampling errors to approach zero, acceptable accuracy can be obtained using the passive strategy for selecting an appropriate sized orifice opening 125 discussed above.

The exhaust sampling system 20 may be controlled to ensure that the instantaneous difference between the total side mass flow and the dilute side mass flow is continually proportional to the power source exhaust mass flow. In order to achieve this, the exhaust gas sampling system controller 22 may be configured to continually monitor the operating characteristics of the power source 10 described above with respect to step 88, and calculate system flow set points which yield proportional sampling. In particular, in transient certification trials in which the power source 10 is challenged to instantaneous changes in exhaust flow rate, the components of the exhaust sampling system 20 may be configured to react to those changes within less than or equal to 500 milliseconds.

The combined flow 37 may pass from the dilution device 54 to the filter 62, whereby the particulates contained within the combined flow 37 may be extracted and trapped within the filter media 61. The filtered combined flow 37 may then pass from the filter 62, through valve 64, and through the flow control valve 74 to the flow sensor 76 where a gravimetric mass determination may be made (step 96). Sensed information may be transmitted from one or more components of the flow sensor 76 to the exhaust sampling system controller 22, and the exhaust sampling system controller 22 may store and/or present the sensed data to the operator or user (step 98).

The combined flow 37 may then pass from the flow sensor 76, through the open valve 78, and to the vacuum 80. The combined flow 37 may exit the exhaust sampling system 20 as illustrated by flow arrow 82. Once an adequate amount of data has been collected and/or stored by the exhaust sampling system controller 22, the exhaust sampling system controller 22 may determine whether or not continued sampling may be required for the purposes of certification (step 102). If continued sampling is required, the exhaust sampling system controller 22 may continue to sense operating characteristics of the power source 10 as described above (step 88). Alternatively, if a sufficient amount of data has been acquired the exhaust sampling system controller 22 may stop sampling (step 104). It is understood that in a transient certification procedure, the user may operate the power source 10 through a variety of different throttle and/or other set points. During such a procedure, the exhaust sampling system 20 may continuously sense the operating characteristics of the power source 10 and may continuously vary the flow rate of the dilute flow 36 delivered to the dilution device 54 in response to the sensed operating characteristics of the power source 10, as well as the sensed flow rate of the combined flow 37 passing through the total side 108 of the exhaust sampling system 20. Because of the complexities involved with an active control over the flow opening area into the sampling system to account for pressure changes during the transient condition, it may be appropriate to conduct testing associated with one transient condition at a time, such as the transient illustrated in FIGS. 6-8 with an appropriate tip 122A-L suited for the particular transient cycle and/or engine/aftertreatment combination being tested.

It is understood that, in an exemplary embodiment, the exhaust sampling system 20 may also be controlled to slow its transient response in applications where a relatively low output power source 10 is connected to a relatively large volume exhaust system, such as, for example, one or more relatively large volume components of the test cell 100. During use, the thermistor 59 may sense changes in the temperature of the exhaust flow 34 and may send the sensed temperature information to the exhaust sampling system controller 22. The exhaust sampling system controller 22 may calculate the volumetric flow rate of the exhaust flow 34 based on, for example, the temperature input received from the thermistor 59 and the mass flow rate of the exhaust flow 34 discussed above. In an exemplary embodiment, the exhaust sampling system controller 22 may calculate the volumetric flow rate at approximately 80 Hz, and the test cell operator may input the volume of the exhaust system based on the length and diameter of, for example, the exhaust line 58. If the time it takes for a particle to travel in the exhaust flow 34 between, for example, the power source 10 and the extraction component 56 exceeds the known response time of the exhaust sampling system 20, the exhaust sampling system controller 22 may delay the proportional response of the exhaust sampling system 20 through control of, for example, the flow control valve 50. For example, if the known response time of the exhaust sampling system 20 is 200 milliseconds and the calculated travel time of a particle between the power source 10 and the extraction component 56 is 300 milliseconds at a given instant, the exhaust sampling system controller 22 may delay a transient response by the exhaust sampling system 20 by 100 milliseconds.

Other embodiments of the disclosed exhaust sampling system 20 will be apparent to those skilled in the art from consideration of the specification. For example, the isolation valve 44 and the valve 78 may be three way valves configured to direct a flow of fluid from a flow line 26 to other locations within the exhaust sampling system 20. In addition, the filter 62 may be fitted with one or more bosses to assist in inserting and/or removing the test filter media cartridge. It is intended that the specification and examples be considered as exemplary only, with the true scope of the invention being indicated by the following claims.

What is claimed is:

1. A method of operating an exhaust sampling system, comprising the steps of:
    determining an expected pressure rise at a test probe location to occur during a specific transient to be tested;
    selecting a flow opening with an L/D ratio responsive to the expected pressure rise;
    flowing exhaust through the flow opening into a test probe positioned in an exhaust stack at the test probe location during an actual testing procedure for the specific transient;
    unrestricting the flow into the test probe responsive to the L/D ratio when a pressure differential between the exhaust stack at a probe location and atmospheric pressure is small at a beginning of the specific transient during the actual testing procedure, but restricting the flow into the test probe responsive to the L/D ratio when the pressure differential is large due to the expected pressure rise during the specific transient of the actual testing procedure.

2. The method of claim 1 wherein the unrestricting step and the restricting step are accomplished passively with the flow opening in an exhaust flow path into the sampling system that acts as an orifice when the pressure differential is large, but not as an orifice when the pressure differential is small;
    sizing the flow opening based upon the expected pressure rise.

3. The method of claim 2 including a step of locating the flow opening at an entrance into the test probe.

4. The method of claim 2 including a step of sizing the flow opening based upon a desired flow rate into the sampling system at a beginning of the specific transient to be tested.

5. The method of claim 4 including a step of measuring a maximum pressure differential at the probe location when an exhaust source connected to the exhaust stack is operated in the specific transient condition prior to the actual testing procedure; and
    setting the expected pressure rise to the measured maximum pressure differential.

6. The method of claim 1 including a step of determining a flow opening size based upon a desired flow rate into the sampling system and the expected pressure rise; and
    attaching a tip with the flow opening size to the test probe.

7. The method of claim 1 including a step of detaching a first tip that defines the flow opening of a first size; and
    attaching a second tip that defines a flow opening of a second size that is different from the first size.

8. A method of reducing over sampling of exhaust with an exhaust sampling system during a transient, comprising the steps of:
    determining an expected pressure rise at a test probe location to occur during a specific transient to be tested;
    selecting a flow opening with an L/D ratio responsive to the expected pressure rise;
    unrestricting flow into the sampling system responsive to the L/D ratio at a beginning of the transient;
    restricting flow into the sampling system responsive to the L/D ratio when pressure at a test probe location increases after a beginning of the transient; and
    the restricting step includes sizing the L/D ratio to be an orifice in a flow path into the test probe when pressure at the test probe location is increasing during the transient.

9. The method of claim 8 including a step of fixing a flow area size of the orifice throughout the transient.

10. The method of claim 9 including a step of setting the flow area size based upon a desired flow rate into the sampling system at the beginning of the transient and the expected pressure rise that occurs at the test probe location during the transient.

11. The method of claim 10 including a step of locating the orifice at an entrance into the test probe.

12. The method of claim 11 including a step of measuring a maximum pressure differential during a transient which corresponds to the transient to be tested prior to performing the actual test procedure; and
    setting the expected pressure rise to the maximum pressure differential.

13. The method of claim 9 including a step of changing the flow area size in the flow path.

14. The method of claim 1 including a step of determining a flow area size based upon a desired flow rate into the sampling system and the expected pressure rise; and
    attaching a tip with the flow area size to the test probe.

15. The method of claim 8 including a step of unrestricting flow into the test probe when pressure at the test probe location is steady prior to the beginning of the transient.

16. A test cell comprising;
    a power source fluidly connected to an exhaust line;
    an exhaust sampling system with a test probe with a flow opening positioned in the exhaust line for receiving exhaust flow originating from the power source;
    the flow opening having an L/D ratio that is selected based upon an expected pressure rise to occur at the test probe during a specific transient to be tested; and wherein the L/D ratio results in a desired unrestricted flow rate into the exhaust sampling system at a beginning of the specific transient to be tested and the L/D ratio resulting in a restricted flow rate into the test probe during the specific transient to be tested responsive to the expected pressure rise.

17. The test cell of claim 16 wherein the test probe includes a detachable tip that defines the flow opening.

18. The test cell of claim 17 including a plurality of interchangeable tips that each define a flow opening having a different flow area size.

19. The test cell of claim 16 wherein the expected pressure rise corresponds to a maximum pressure differential between pressure at a test probe location and atmospheric pressure during the specific transient to be tested.

* * * * *